United States Patent [19]

Bluestone et al.

[11] B 4,001,325

[45] Jan. 4, 1977

[54] α-CHLOROACETANILIDE SELECTIVE HERBICIDES

[75] Inventors: Henry Bluestone, Beachwood; James A. Scozzie, Willoughby Hills; Joseph A. Ignatoski, Mentor, all of Ohio

[73] Assignee: Diamond Shamrock Corporation, Cleveland, Ohio

[22] Filed: Nov. 6, 1973

[21] Appl. No.: 413,379

[44] Published under the second Trial Voluntary Protest Program on March 9, 1976 as document No. B 413,379.

Related U.S. Application Data

[63] Continuation-in-part of Ser. No. 316,408, Dec. 18, 1972, abandoned.

[52] U.S. Cl. .............................. 260/562 B; 71/118
[51] Int. Cl.$^2$ ............................. C07C 103/365
[58] Field of Search .............................. 260/562

[56] References Cited

UNITED STATES PATENTS

| | | |
|---|---|---|
| 3,268,584 | 8/1966 | Olin .............................. 260/562 |
| 3,403,994 | 10/1968 | Olin .............................. 260/562 |
| 3,442,945 | 5/1969 | Olin .............................. 260/562 |
| 3,475,156 | 10/1969 | Olin .............................. 260/562 |
| 3,475,157 | 10/1969 | Olin .............................. 260/562 |
| 3,535,377 | 10/1970 | Steinbrunn et al. .............. 260/562 |

OTHER PUBLICATIONS

Chupp et al., J. Org. Chem., vol. 34, pp. 1192–1197 (1969).

Wolf et al., Liebigs Annelen Der Chemie, vol. 626, pp. 47–60 (1959).

Primary Examiner—Harry I. Moatz
Attorney, Agent, or Firm—Helen P. Brush

[57] ABSTRACT

Compositions containing an α-chloroacetanilide compound of the formula wherein $R^1$ is selected from the group consisting of primary and secondary alkyl radicals of 1–3 carbon atoms and $R^2$ is selected from the group consisting of hydrogen and primary and secondary alkyl radicals of 2–3 carbon atoms, are useful for protecting various agronomic crops from undesirable weed infestation. Presently preferred because of their optimum selective herbicidal activity are those compounds wherein $R^1$ of the above structure is either methyl or ethyl and $R^2$ is ethyl.

2 Claims, No Drawings

α-CHLOROACETANILIDE SELECTIVE HERBICIDES

BACKGROUND OF THE INVENTION

This application is a continuation-in-part of our co-pending application, Ser. No. 316,408, filed Dec. 18, 1972, and now abandoned.

This invention relates to certain N-propargyl-chloroacetanilides having herbicidal activity, particularly as selective herbicides for agronomic crops such as corn, soybeans, peanuts, and the like, and to their preparation. This invention further relates to herbicidal compositions and to methods for controlling or modifying the growth of plant systems.

The herbicidal effectiveness of ring substituted α-haloacetanilide compounds, as a class, has already been reported in numerous U.S. and foreign patents, e.g., in U.S. Pat. No. Re 26,961 and in U.S. Pat. Nos. 3,268,584; 3,442,945; 3,475,156; 3,535,377; 3,547,620; 3,630,716; and 3,637,847, among others. In particular, U.S. Pat. Nos. 3,442,945 and 3,475,156 disclose that α-haloacetanilides having a tertiary alkyl radical of at least four carbon atoms on the phenyl ring in the ortho position with respect to the amide nitrogen atom have particularly efficacious herbicidal properties.

It has now been found that a novel group of 2-chloro-N-propargylacetanilide compounds which conform to the foregoing structure likewise possess excellent herbicidal properties and are useful for selectively controlling undesirable plant growth in certain agronomic crops.

SUMMARY OF THE INVENTION

Accordingly, the present invention is directed to 2-chloro-N-propargylacetanilides corresponding to the formula

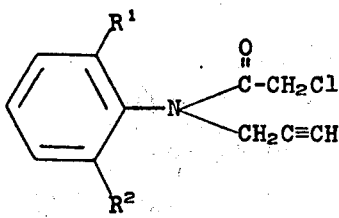

wherein $R^1$ is selected from the group consisting of primary and secondary alkyl radicals of 1–3 carbon atoms and $R^2$ is selected from the group consisting of hydrogen and primary and secondary alkyl radicals of 2–3 carbon atoms.

These compounds are effective particularly as pre-emergence herbicides for the control of dicotyledonous weed species, i.e., broadleaf plants, and especially the monocotyledonous species such as grassy-type weeds. Most importantly, these compounds effectively control undesirable plant growth in desirable crops without causing injury to the crops themselves.

The preparation of these compounds and their herbicidal use is specifically illustrated below.

DESCRIPTION OF PREFERRED EMBODIMENTS

Specific 2-chloro-N-propargylacetanilide compounds of this invention include the following:
2-chloro-2'-methyl-6'-ethyl-N-propargylacetanilide
2-chloro-2',6'-diethyl-N-propargylacetanilide
2-chloro-2'-methyl-N-propargylacetanilide
2-chloro-2'-ethyl-N-propargylacetanilide
2-chloro-2',6'-diisopropyl-N-propargylacetanilide
2-chloro-2'-methyl-6'-isopropyl-N-propargylacetanilide
2-chloro-2'-ethyl-6'-isopropyl-N-propargylacetanilide
2-chloro-2'-isopropyl-N-propargylacetanilide.

Of these, 2-chloro-2',6'-diethyl-N-propargylacetanilide and 2-chloro-2'-methyl-6'-ethyl-N-propargylacetanilide are particularly preferred at present because of their excellent selective herbicidal effectiveness, i.e., they control undesirable plant species at rates of application which exert no injury to the desirable crop itself.

The compounds of this invention generally may be prepared by reacting the appropriate substituted N-propargylaniline with approximately an equimolar quantity of either the anhydride or chloride of chloroacetic acid, which reaction preferably is conducted in the presence of an acid scavenger. The product is isolated and purified by recrystallization from suitable solvents.

The alkyl-substituted N-propargylaniline intermediates for preparing the compounds of this invention generally have not been reported heretofore and are not commercially available at the present time. However, these compounds may be prepared according to a known procedure which involves reacting equimolar quantities of the appropriate substituted aniline and propargyl bromide in an alkanol solvent under alkaline conditions, e.g., in the presence of an alkali metal carbonate, for a time period of 15 hours, preferably longer. As shown hereinafter by specific examples, moderate yields, e.g., 29–40%, of the desired N-propargylaniline compounds usually are obtained from this reaction.

By reacting the substituted aniline and propargyl bromide in the absence of solvent or an alkali metal carbonate and by utilizing a large excess of the aniline, i.e., 3–4 moles per each mole of the bromide, improved yields, i.e., greater than 50% of the desired N-propargylaniline compounds can be realized in reaction times of only 4–8 hours. Likewise, the formation of undesirable by-products such as the corresponding N,N-dipropargylanilines is minimized. Preparation of substituted N-propargylaniline compounds by this improved procedure is shown hereinafter by specific examples.

The alkyl-substituted 2-chloro-N-propargylacetanilide compounds of the invention are either oily liquids or crystalline solids. They generally have less than 5% solubility in water and varying degrees of solubility in many common organic solvents.

References may also be made to the examples for a fuller understanding of the invention. The infrared spectrum for each product described below is consistent with the assigned structure. All percentages, parts, and quantities given other than volume proportions are by weight unless otherwise indicated.

EXAMPLES 1–6

Preparation of 2,6-Diethyl-N-propargylaniline Intermediate

A reactor equipped with a thermometer, stirrer, $N_2$ inlet and outlet tubes and reflux condenser fitted with a drying tube is charged with 74.5 g (0.5 mole) of 2,6- diethylaniline, 71.4 g (0.6 mole) of propargyl bromide, 41.4 g (0.3 mole) of anhydrous potassium carbonate, and 125 ml of absolute ethanol. The mixture is refluxed for 18 hours under slight positive $N_2$ pressure. The reaction mixture is cooled and additional potassium carbonate is added until the solution is weakly basic. It is then transferred to a separatory funnel. The supernatant organic layer which develops is isolated and dried over anhydrous potassium carbonate. The liquid is then separated by filtration and the solvent stripped in vacuo. The residue remaining is vacuum distilled. The clear liquid product (17.6 g) is approximately 90% pure 2,6-diethyl-N-propargylaniline as indicated by vapor phase chromatography. It has a boiling point of 86°–88° C at 0.6–0.7 mm Hg pressure. The impurities are 2,6-diethylaniline and 2,6-diethyl-N,N-dipropargylaniline.

Table 1 gives data on this compound as well as other novel alkyl-substituted N-propargylaniline intermediates prepared accordingly by reacting equimolar quantities of the corresponding alkyl-substituted aniline and propargyl bromide. The data in the table include the alkyl-substituted N-propargylaniline product, its boiling point (°C) and percent yield.

TABLE 1

| Example | Product | Reaction Time hours | Boiling Point °C/mm Hg | % Yield Product[1] |
|---|---|---|---|---|
| 1 | 2,6-Diethyl-N-propargylaniline | 18 | 86–88/0.6–0.7 | 20 |
| 2 | 2-Methyl-N-propargylaniline | 17 | —[2] | &—[2] |
| 3 | 2-Methyl-6-isopropyl-N-propargylaniline | 96 | 76/0.25 | & 21.5 |
| 4 | 2,6-Diisopropyl-N-propargylaniline | 48 | 127/8.5 | 17.9 |
| 5 | 2-Ethyl-6-isopropyl-N-propargylaniline | 90 | 88/0.5 | 47.5 |
| 6 | 2-Ethyl-N-propargylaniline | 72 | 108/3.2 | 25.6 |

[1]Product purity ≧ 90%
[2]Product not isolated in pure form.

EXAMPLES 7 and 8

In these examples, the reaction between the appropriate alkyl-substituted aniline and propargyl bromide is conducted as generally outlined in the preceding examples, except that the alcohol solvent and the carbonate are not employed. Likewise, the molar ratio of aniline to bromide reacted is 4:1. Results obtained are as follows:

TABLE 2

| Ex. | Product | Reaction Time hours | Boiling Point °C/mm Hg | % Yield |
|---|---|---|---|---|
| 7 | 2-Methyl-6-ethyl- | 6 | 102/1.4 | 59[1] |
| 8 | N-propargylaniline 2-Isopropyl-N-propargylaniline | 4 | —[2] | 75 |

[1]This reaction conducted according to Example 1 for 120 hours gives only 31% yield.
[2]Not recorded.

EXAMPLES 9–16

Preparation of 2-Chloro-2',6'-diethyl-N-propargylacetanilide

The above-identified compound of this invention is prepared as follows:

A reactor is charged with 7.0 g (0.034 mole) of 2,6-diethyl-N-propargylaniline (Product of Example 1), 100 ml of ethyl acetate and 5.75 g (0.034 mole) of chloroacetic anhydride. This reaction mixture is heated at reflux for 1.5 hours, after which the solvent is stripped from the mixture. The residue is distilled to give 5.6 g of a cream-colored oil which solidifies on standing. This product is identified as 2-chloro-2',6'-diethyl-N-propargylacetanilide by elemental analytical data as shown in Table 3 below.

Following the general procedure as outlined above, other compounds of the invention are prepared by reacting the appropriate N-propargylaniline (Products of previous Examples 2–8) with either a chloroacetic acid anhydride or chloride. In each instance, the reaction is conducted in an appropriate solvent in the presence of an acid scavenger, followed by solvent stripping and purification of the crude product.

Table 3 below gives data for the compounds prepared, including either the melting point (°C) or boiling point (°C), the % yield and analysis as % C, H, and N for each compound.

TABLE 3

| Example | Product | % Yield | Melting Point °C | Boiling Point °C/mm Hg | Elemental Analysis Calc. % | | Found % | |
|---|---|---|---|---|---|---|---|---|
| 9 | 2-Chloro-2',6'-diethyl-N-propargylacetanilide | 63 | — | 138–142/ 0.15 | C | 68.3 | C | 68.1 |
|   |   |   |   |   | H | 6.9 | H | 6.9 |
|   |   |   |   |   | N | 5.3 | N | 5.4 |
| 10 | 2-Chloro-2'-methyl-N-propargylacetanilide | 75 | — | 111–117/ 0.02–0.03 | C | 65.0 | C | 64.5 |
|   |   |   |   |   | H | 5.5 | H | 5.4 |
|   |   |   |   |   | N | 6.3 | N | 6.5 |
| 11 | 2-Chloro-2'-ethyl-N-propargylacetanilide | 83 | 76–78 | — | C | 66.2 | C | 66.6 |
|   |   |   |   |   | H | 6.0 | H | 6.0 |
|   |   |   |   |   | N | 5.9 | N | 6.1 |
| 12 | 2-Chloro-2'-methyl-6'-isopropyl-N-propargyl- | 49.7 | 69–70 | — | C | 68.3 | C | 69.9 |
|   |   |   |   |   | H | 6.9 | H | 7.1 |

TABLE 3-continued

| Example | Product | % Yield | Melting Point °C | Boiling Point °C/mm Hg | Elemental Analysis Calc. % | | Found % | |
|---|---|---|---|---|---|---|---|---|
| | acetanilide | | | | N | 5.3 | N | 5.4 |
| 13 | 2-Chloro-2',6'-diiso-propyl-N-propargyl-acetanilide | 25 | 93–98 | — | C<br>H | 70.0<br>7.6 | C<br>H | 69.6<br>7.4 |
| 14 | 2-Chloro-2'-ethyl-6'-isopropyl-N-propargyl-acetanilide | 25.4 | 53–54 | — | N<br>C<br>H<br>N | 4.8<br>69.2<br>7.3<br>5.0 | N<br>C<br>H<br>N | 4.5<br>69.5<br>6.9<br>4.8 |
| 15 | 2-Chloro-2'-methyl-6'-ethyl-N-propargyl-acetanilide | 69 | — | 123–126/0.06 | C<br>H<br>N | 67.3<br>6.5<br>5.6 | C<br>H<br>N | 67.4<br>6.5<br>5.6 |
| 16 | 2-Chloro-2'-isopropyl-N-propargylacetanilide | 65.6 (crude) | 112–115 | — | C<br>N | 67.3<br>5.6 | C<br>N | 66.8<br>5.4 |

For herbicidal application, the 2-chloro-N-propargylacetanilide compounds of this invention can conceivably be used in undiluted form. It is frequently desirable, however, to apply them in admixture with at least one herbicide conditioning agent, i.e., a liquid or solid inert, pesticidal carrier or adjuvant in the form of solutions, emulsions, suspensions, or dusts.

For the preparation of solutions for direct spraying, medium to high boiling mineral oil fractions, coal tar oils, oils of vegetable and animal origin, and polycyclic hydrocarbons such as naphthalene derivatives are suitable.

Aqueous formulations may be prepared by adding water to emulsifiable concentrates, pastes, or wettable powders of the active ingredients. Emulsions are prepared, e.g., by dissolving an active ingredient in a solvent and homogenizing the resulting solution in water by means of wetting or dispersing agents. Concentrates are prepared from active ingredient, emulsifying agent, and possibly solvent. Dusts (or wettable powders) are obtained by mixing or grinding the active ingredient with a solid carrier.

The herbicidal compositions of this invention may also contain other compatible growth regulants, fertilizers, spray oils, etc., according to common practice in herbicide formulating art at the present time. In general, the herbicidal compositions of the invention may contain from 0.01% to about 99% by weight of an alkyl-substituted 2-chloro-N-propargylacetanilide compound as the active ingredient.

Undesirable plant growth is regulated by applying a herbicidally-active amount of a substituted 2-chloro-N-propargylacetanilide to the plant locus. When used as a preemergent herbicide, a compound or formulations thereof usually are applied to the soil prior to plant emergence. The herbicide, usually in formulation, is applied directly to the plant foliage when used as a postemergent herbicide.

An alkyl-substituted 2-chloro-N-propargylacetanilide compound of this invention is effective as a preemergent herbicide when applied generally at rates ranging from about 0.25 to about 8 lbs/A (pounds per acre), and in most instances provides satisfactory control when applied at rates from about 0.5 to about 4 lbs/A.

Greenhouse Preemergence Herbicide Tests

To illustrate the preemergence herbicidal efficiency of the alkyl-substituted 2-chloro-N-propargylacetanilides of this invention, test formulations are prepared of each compound by mixing 20 ml of an acetone solution containing 0.125 g of chemical with 20 ml of water containing 0.01 g of Triton X-155 surfactant. The resultant formulations contain 3125 ppm of test compound, 50% by volume of acetone and 0.025% by weight of surfactant. Appropriate lower concentrations are obtained by diluting this formulation with surfactant-acetone solution so that the concentration of adjuvants is maintained at the original levels.

Seeds of three broadleaf and three grass species are planted in soil contained in 10 inch × 8 inch × 3 inch aluminum pans filled with 1.5 inches of composted soil. The broadleaf species are pigweed (*Amaranthus retroflexus*), velvetleaf (*Abutilon theophrasti*), and morning-glory (*Ipomea coccinea*); the grasses are red millet (*Panicum milliacem*), green foxtail (*Setaria viridis*) and Japanese millet (*Echinochloa frumentacea*).

The seeded pans are sprayed so that the soil surface is uniformly covered with dilutions of the stock formulation providing dosage rates of the test compounds as shown in the following table.

Two weeks after treatment, percent control (plant kill) at each dosage rate is estimated with results as follows:

TABLE 4

| Test Compound | Dosage lb/A | % Control Broadleaves | Grasses |
|---|---|---|---|
| Product of Ex.: | | | |
| 9 | 1.0 | 35 | 95 |
| | 0.5 | 35 | 90 |
| | 0.25 | 0 | 95 |
| | 0.125 | 0 | 95 |
| | 0.062 | 0 | 85 |
| 10 | 1.0 | 35 | 90 |
| | 0.5 | 0 | 80 |
| | 0.25 | 0 | 85 |
| | 0.125 | 0 | 55 |
| | 0.062 | 0 | 0 |
| 11 | 1.0 | 35 | 95 |
| | 0.5 | 0 | 90 |
| | 0.25 | — | 80 |
| | 0.125 | — | 55 |
| | 0.062 | — | 0 |
| 12 | 2.0 | 40 | 90 |
| | 1.0 | 0 | 90 |
| | 0.5 | — | 70 |
| | 0.125 | — | 65 |
| | 0.062 | — | 45 |
| 13 | 1.0 | 0 | 90 |
| | 0.5 | — | 90 |
| | 0.25 | — | 50 |
| | 0.125 | — | 20 |
| 14 | 1.0 | 0 | 100 |
| | 0.5 | — | 80 |
| | 0.25 | — | 40 |
| | 0.125 | — | 40 |
| 15 | 1.0 | 35 | 99 |
| | 0.5 | 0 | 98 |
| | 0.25 | — | 85 |
| | 0.125 | — | 70 |
| | 0.062 | — | 0 |
| 16 | 1.0 | 0 | 100 |
| | 0.5 | — | 90 |
| | 0.25 | — | 80 |

These results indicate that minimum dosages of the compounds of this invention are effective for controlling growth of grassy weed species.

Field Preemergence Test

Test plots of fertilized, light sandy soil containing 0.7% organic matter are sprayed uniformly with aqueous suspensions prepared from emulsifiable concentrates containing 12%, by weight, of the test chemicals diluted to provide dosage rates of the test compounds corresponding to 2.0, 1.0, 0.5, and 0.25 pound per acre (lb/A). The plots are then sown with seeds of the following crop plants: sweet corn, cotton (Coker 413) and soybeans, var. Davis. Seeds of the following weed plants are planted: redroot pigweed, prickly sida, common lambsquarter, goosegrass and giant foxtail.

Three to four weeks after planting, percent control (plant kill) of the test plants is estimated, from a rating of 0 which denotes no injury to the plant up to 100 which denotes complete destruction. The herbicidal action of the test compounds obtained on the weed species is as follows:

The above results indicate that at the minimum dosages applied, the test compounds provide commercially acceptable control (> 80%) of the weed species with the exception of prickly sida. Crop tolerance at these dosages, likewise being greater than 80%, is also acceptable in commercial application.

EXAMPLE 17

This example illustrates the selective herbicidal activity of two of the presently preferred compounds of this invention against various weed species in a corn crop.

Plots of light sandy soil, cleared of all weeds, are uniformly treated with aqueous dispersions prepared from an emulsifiable concentrate containing 2–4 pounds of active ingredient per gallon. Diluted aqueous dispersions are applied as surface treatments at 2.0, 1.0, 0.5, and 0.25 pound of active ingredient per acre (lb/A).

TABLE 5(A)

| Test Compound | Dosage lb/A | % Weed Control | | | | |
|---|---|---|---|---|---|---|
| | | Redroot Pigweed | Prickly Sida | Giant Foxtail | Goosegrass | Common Lambsquarter |
| Product of Ex.: | | | | | | |
| 9 | 2.0 | 100 | 93 | 100 | 100 | 100 |
| | 1.0 | 100 | 42 | 97 | 100 | 100 |
| | 0.5 | 93 | 80 | 85 | 98 | 100 |
| | 0.25 | 75 | 0 | 42 | 94 | 95 |
| 10 | 2.0 | 67 | 25 | 80 | 97 | 95 |
| | 1.0 | 45 | 0 | 70 | 92 | 95 |
| | 0.5 | 27 | 0 | 20 | 78 | 60 |
| | 0.25 | 0 | 0 | 0 | 53 | 40 |
| 11 | 2.0 | 98 | 57 | 90 | 100 | 100 |
| | 1.0 | 80 | 33 | 45 | 100 | 100 |
| | 0.5 | 75 | 13 | 23 | 82 | 70 |
| | 0.25 | 33 | 0 | 0 | 62 | 50 |
| 15 | 2.0 | 100 | 97 | 100 | 100 | 100 |
| | 1.0 | 100 | 93 | 97 | 100 | 100 |
| | 0.5 | 89 | 55 | 78 | 97 | 98 |
| | 0.25 | 65 | 0 | 47 | 87 | 95 |

Phytotoxic effects observed on the crop species is estimated with results as follows:

TABLE 5(B)

| Test Compound | Dosage lb/A | % Crop Kill | | |
|---|---|---|---|---|
| | | Corn | Cotton | Soybeans |
| Product of Ex.: | | | | |
| 9 | 2.0 | 3 | 3 | 0 |
| | 1.0 | 0 | 0 | 0 |
| 10 | 2.0 | 0 | 3 | 0 |
| | 1.0 | 0 | 3 | 0 |
| | 0.5 | 0 | 0 | 0 |
| 11 | 2.0 | 0 | 18 | 3 |
| | 1.0 | 0 | 10 | 0 |
| | 0.5 | 0 | 0 | 0 |
| 15 | 2.0 | 12 | 13 | 13 |
| | 1.0 | 3 | 6 | 3 |
| | 0.5 | 0 | 0 | 0 |

The treated test plots are sown to corn and with seeds of the following weed species:

A. Broadleaves morningglory (*Ipomoea sp.*)
velvetleaf (*Abutilon theophrasti*)

B. Grasses barnyardgrass (*Echinochloa crusgalli*)
yellow foxtail (*Setaria lutescens*)
fall panicum (*Panicum dichotomiflorum*)
Johnsongrass (*Sorghum halepense*)
goosegrass (*Eleusine indica*)

Three to four weeks after planting, the degree of damage to both the corn stands and the weed plants is assessed from a rating of 0% (no injury) to 100% (complete destruction). The results obtained are as follows:

TABLE 6

| Test Compound | Dosage lb/A | % Weed Kill | | | | | | |
|---|---|---|---|---|---|---|---|---|
| | | Morning-glory | Velvet-leaf | Barnyard-grass | Yellow Foxtail | Fall Panicum | Johnson-grass | Goose-grass |
| Product of Ex. 9 | 2.0 | 3 | 18 | 100 | 100 | 100 | 100 | 100 |
| | 1.0 | 0 | 6 | 98 | 100 | 95 | 80 | 100 |
| | 0.5 | 0 | 0 | 98 | 95 | 88 | 37 | 100 |
| | 0.25 | 0 | 0 | 68 | 80 | 73 | 0 | 87 |
| Product of Ex. 15 | 2.0 | 6 | 80 | 100 | 100 | 100 | 100 | 100 |
| | 1.0 | 0 | 37 | 100 | 100 | 97 | 100 | 100 |
| | 0.5 | 0 | 27 | 100 | 97 | 96 | 73 | 100 |
| | 0.25 | 0 | 0 | 88 | 82 | 78 | 0 | 82 |

2-Chloro-2',6'-diethyl-N-propargylacetanilide compound (the product of Example 9) shows no phytotoxic effects on corn when applied at a dosage rate of 2 lb/A. The product of Example 15, 2-chloro-2'-methyl-6'-ethyl-N-propargylacetanilide, exerts no injury to the corn at a dosage rate of 1 lb/A.

At dosages of each of these compounds which are nonharmful to the corn crop, excellent control of the grassy weeds is provided with fair control of one of the broadleaf species, particularly by the product of Example 15.

EXAMPLE 18

To further illustrate the herbicidal activity of compounds of this invention in different types of soil as would be encountered in different crop growing localities, a preemergence herbicide test is conducted generally as outlined previously herein. Two light sandy soils are employed containing 0.7% and 1.8% organic matter (O.M.), respectively, along with two loam-type, heavier soils containing either 2.0% or 5–5.5% organic matter (O.M.).

The test plots are all sprayed uniformly with formulations of the test compounds providing 2.0, 1.0, 0.5, and 0.25 pound of active chemical per acre (lb/A).

Prior to treatment, the soil plots are sown to field corn, soybean, and grain sorghum crops and seeds of barnyard-grass and yellow foxtail.

Three weeks after planting, the percent control of plant growth is rated from 0% (no injury) to 100% (total destruction). The results obtained are as follows:

TABLE 7(A)

| Test Compound | Dosage lb/A | % CONTROL | | | | | | | |
|---|---|---|---|---|---|---|---|---|---|
| | | Sand – 0.7% O.M. | | Sand – 1.8% O.M. | | Medium Soil – 2.0% O.M. | | Heavy Soil – 5–5.5% O.M. | |
| | | Barnyard-grass | Yellow Foxtail | Barnyard-grass | Yellow Foxtail | Barnyard-grass | Yellow Foxtail | Barnyard-grass | Yellow Foxtail |
| Product of Example 9 | 2.0 | 100 | 100 | 100 | 100 | 100 | 100 | 100 | 100 |
| | 1.0 | 90 | 70 | 90 | 80 | 100 | 100 | 98 | 100 |
| | 0.5 | 60 | 50 | 85 | 85 | 95 | 90 | 90 | 90 |
| Product of Example 15 | 2.0 | 99 | 90 | 99 | 85 | 100 | 100 | 100 | 100 |
| | 1.0 | 99 | 65 | 90 | 65 | 100 | 100 | 100 | 100 |
| | 0.5 | 75 | 45 | 50 | 30 | 100 | 100 | 98 | 98 |

Phytotoxic effects on the crop stands are similarly rated with the following results:

TABLE 7(B)

| Test Compound | Dosage lb/A | % PHYTOTOXICITY | | | | | | | | | | | |
|---|---|---|---|---|---|---|---|---|---|---|---|---|---|
| | | Sand – 0.7% O.M. | | | Sand – 1.8% O.M. | | | Medium Soil – 2.0% O.M. | | | Heavy Soil – 5–5.5% O.M. | | |
| | | Corn | Soybeans | Sorghum | Corn | Soybeans | Sorghum | Corn | Soybeans | Sorghum | Corn | Soybeans | Sorghum |
| Product of Ex. 9 | 2.0 | 0 | 0 | 30 | 0 | 0 | 70 | 10 | 0 | 95 | 10 | 0 | 99 |
| | 1.0 | 0 | 0 | 10 | 0 | 0 | 30 | 0 | 0 | 55 | 0 | 0 | 75 |
| | 0.5 | 0 | 0 | 0 | 0 | 0 | 10 | 0 | 0 | 40 | 0 | 0 | 35 |
| Product of Ex. 15 | 2.0 | 10 | 0 | 50 | 0 | 0 | 90 | 55 | 0 | 100 | 10 | 0 | 99 |
| | 1.0 | 0 | 0 | 15 | 0 | 0 | 65 | 10 | 0 | 100 | 0 | 0 | 90 |
| | 0.5 | 0 | 0 | 0 | 0 | 0 | 20 | 0 | 0 | 60 | 0 | 0 | 45 |

As indicated by the foregoing results, the test compounds exert excellent control of the grassy weeds in the heavier soils at dosages of 0.5 pound active chemical per acre. At these rates, no phytotoxic effects are observed on either the corn or soybean plants. However, both compounds are nonselective on sorghum, exerting noticeable phytotoxicity on this crop even when applied at 0.5 lb/A.

In sandy soils, the test compounds provide effective grassy weed control. They exert minimal, if any, phytotoxic effects on the corn and soybean crops, while being moderately injurious to sorghum.

It is to be understood that although the invention has been described with specific reference to particular embodiments thereof, it is not to be so limited, since changes and alterations therein may be made which are within the full intended scope of this invention as defined by the appended claims.

We claim:
1. 2-Chloro-2',6'-diethyl-N-propargylacetanilide.
2. 2-Chloro-2'-methyl-6'-ethyl-N-propargylacetanilide.

* * * * *